United States Patent [19]

Carlson et al.

[11] Patent Number: 5,701,908
[45] Date of Patent: Dec. 30, 1997

[54] SYSTEM AND METHOD FOR MONITORING AND CONTROLLING THE TEMPERATURE OF A CATHETER-MOUNTED HEATER

[75] Inventors: Gary D. Carlson, Newport Beach; Mark Minot, Aliso Viejo, both of Calif.

[73] Assignee: Baxter International Inc., Deerfield, Ill.

[21] Appl. No.: 747,099

[22] Filed: Nov. 8, 1996

Related U.S. Application Data

[60] Division of Ser. No. 422,369, Apr. 14, 1995, Pat. No. 5,634,470, which is a continuation-in-part of Ser. No. 268,217, Jun. 29, 1994, Pat. No. 5,636,638.

[51] Int. Cl.[6] ................................. A61B 5/028
[52] U.S. Cl. ................................. 128/713
[58] Field of Search ........................ 128/637, 691, 128/692, 713

[56] References Cited

U.S. PATENT DOCUMENTS

| | | |
|---|---|---|
| 3,614,589 | 10/1971 | Ireland et al. . |
| 3,638,656 | 2/1972 | Grandjean et al. . |
| 4,004,576 | 1/1977 | Gahwiler et al. . |
| 4,140,133 | 2/1979 | Kastrubin et al. . |
| 4,216,462 | 8/1980 | McGrath et al. . |
| 4,317,165 | 2/1982 | Sullivan . |
| 4,448,202 | 5/1984 | Wajszczuk et al. . |
| 4,467,813 | 8/1984 | Schomburg . |
| 4,507,974 | 4/1985 | Yelderman . |
| 4,574,342 | 3/1986 | Runyan . |
| 4,677,986 | 7/1987 | DeCote, Jr. . |
| 4,728,881 | 3/1988 | Evans et al. . |
| 4,912,394 | 3/1990 | Sugimoto et al. . |
| 4,951,682 | 8/1990 | Petre . |
| 5,003,983 | 4/1991 | Dingwall et al. . |
| 5,003,991 | 4/1991 | Takayama et al. . |
| 5,014,284 | 5/1991 | Langer et al. . |
| 5,056,526 | 10/1991 | Khalil . |
| 5,089,768 | 2/1992 | Sato . |
| 5,146,414 | 9/1992 | McKown et al. . |
| 5,242,440 | 9/1993 | Shippert . |
| 5,304,206 | 4/1994 | Baker, Jr. et al. . |
| 5,305,760 | 4/1994 | McKown et al. . |
| 5,342,356 | 8/1994 | Ellman et al. . |
| 5,366,483 | 11/1994 | Sadkhin . |

FOREIGN PATENT DOCUMENTS

| | | |
|---|---|---|
| 2511-560 | 11/1981 | France . |
| 2222685 | 3/1990 | United Kingdom . |
| WO93/15652 | 8/1993 | WIPO . |
| WO93/15654 | 8/1993 | WIPO . |

OTHER PUBLICATIONS

B. Ross, M. Hoke, *Preamplifier with Digitally Controlled Automatic Offset Compensation Circuit for Physiological Applications*, Scand. Audio. Suppl. 11, 1980.

*Primary Examiner*—William E. Kamm
*Assistant Examiner*—George R. Evanisko
*Attorney, Agent, or Firm*—Bruce M. Canter; Guy L. Cumberbatch

[57] ABSTRACT

A system for monitoring and controlling a temperature of a heating element in a thermodilution catheter to maintain it within safe physiological limits includes a calibration circuit, a device for controlling the supply of power to the system, a relay between the calibration circuit and the heating element for switching power therebetween, a transistorized voltage detecting circuit for determining whether power has been supplied to the calibration circuit, and a device responsive to transistorized voltage detecting circuit to remove power from the system. Also, a method for monitoring and controlling a temperature of a thermodilution catheter-mounted heating element including providing a calibration circuit, switching a supply of power to either the calibration circuit or the heating element, monitoring the supply of power to the calibration circuit, and removing power from either the calibration circuit or the heating element in response to the monitored power at the calibration circuit.

28 Claims, 8 Drawing Sheets

SYSTEM AND METHOD FOR MONITORING AND CONTROLLING THE TEMPERATURE OF A CATHETER-MOUNTED HEATER

RELATED CASES

This application is a divisional of U.S. application Ser. No. 08/422,369, filed on Apr. 14, 1995, now U.S. Pat. No. 5,634,470 which is a continuation-in-part of U.S. application Ser. No. 08/268,217, filed on Jun. 29, 1994 now U.S. Pat. No. 5,636,638.

This application is a continuation-in-part of U.S. application Ser. No. 08/268,217, filed on Jun. 29, 1994, for Electrical Power Amplifier For Continuous Cardiac Output Monitoring, which is incorporated herein by reference as though fully set forth.

BACKGROUND OF THE INVENTION

1. Field of the Invention

This invention relates generally to thermodilution catheters of the type that have a heating element which applies heat to a patient's blood for the purpose of measuring a physiological condition, such as volumetric blood flow. More specifically, the invention relates to systems and methods for controlling the application of power to the heating element in order to prevent harm to the patient or damage to the catheter.

2. Description of the Prior Art

It has recently become known in the art that cardiac output can be continuously measured by utilizing a heating element on a thermodilution catheter. By applying a known thermal signal on a regular or continuous basis, cardiac output measurements can be made continuously by detecting the thermal signal downstream from the input signal and by applying sophisticated signal processing techniques. One such cardiac output measurement system is disclosed in U.S. Pat. No. 4,507,974 to Yelderman which discloses the use of a heat signal which is generated according to a pseudo-random binary sequence (PRBS). Correlation techniques are then used at the downstream position to extract the flow rate of the blood. An improved version of this system is disclosed in U.S. Pat. No. 5,146,414 to McKown, et al. The McKown et al. patent discloses a recursive or adaptive processor and uses the lagged normal model for the cardiac system in order to enhance the signal to noise ratio of the sensed downstream thermal signal.

In order for a heating element to be utilized on or in a catheter that is to be placed in a human body, certain safety requirements must be met. Most importantly, the heating element must be controlled to insure that it is operating within certain acceptable temperature ranges. Additionally, certain fail-safe mechanisms must be utilized to insure that the heating element does not get too hot. In addition to the normal temperature controls, it would be useful to be able to determine when the heating element is either subject to low flow conditions, operating in air, or otherwise under operating conditions wherein any excess heat is not being adequately dissipated.

One such prior art thermodilution heating element catheter utilizes a resistive heater having a known thermal coefficient of resistance. By monitoring the patient's blood temperature and the heating element resistance it is possible to monitor and automatically control the temperature and heat output of the heating element temperature. Certain embodiments of such a resistive heater thermodilution catheter and heater control system are disclosed in the following related U.S. patent applications: Ser. No. 08/049,231, to Quinn, et al., Ser. No. 08/245,727, to Yelderman et al., and Ser. No. 08/334,443, to McKown et al, (hereinafter collectively referred to as Quinn et al.) assigned to Interflo Medical, Inc., and incorporated herein by reference as though fully set forth. In alternate systems, a thermistor or thermometer is used in conjunction with the heater in order to continuously monitor the temperature of the heating element.

The catheter heating element disclosed in Quinn et al. has proven to be very safe in that it provides a means to continuously monitor and automatically control the application of power to the heating element, thereby controlling its temperature. Certain fail-safe systems have thus been incorporated into a heat-based continuous cardiac output system which utilizes the teachings of Quinn et al. An example of such a system was marketed in the VIGILANCE® cardiac output monitor marketed and sold by Baxter Healthcare Corporation, a subsidiary of Baxter International, Inc., the assignee of the present invention. The VIGILANCE® system incorporates certain fail-safe mechanisms in order to avoid the application of excessive heat to the patient's bloodstream. These fail-safe mechanisms come into play when the heating element rises above a certain predetermined temperature level.

Although the use of the Quinn et al. catheter in conjunction with the VIGILANCE® system has proven to be safe for human clinical use, there would be further utility in being able to determine, more swiftly and redundantly, when the heating element catheter is operating in very low flow conditions or in "no flow" conditions outside of the human body. Although the VIGILANCE® system provides for reducing power to the heating element when it reaches or exceeds its predetermined temperature level in order to prevent damage to the patient, it would be useful to provide a redundant control of the heating element under low flow conditions while the catheter is present in the patient's body.

It would also be useful to reduce power to the heating element while the catheter is outside the patient's body. For example, just prior to calibration of the VIGILANCE® system, power is supplied to a calibration circuit. If power is inadvertently supplied to the heating element while the catheter is under a zero flow condition outside the patient's body, it could result in thermal deformation in the catheter tubing in the region of the heating element.

It would also be useful to know, while the catheter was in the patient's body, that power being applied to the system was not going to the heating element, but was instead going to other parts of the system, such as the calibration circuit or resistor.

SUMMARY OF THE INVENTION

Accordingly, it is an object of the invention to provide a system for monitoring and controlling the temperature of a thermodilution catheter heating element within safe physiological limits and under various conditions and environments.

It is a further object of the invention to automatically reduce power to the heating element under low flow or zero flow conditions.

It is a further object of the invention to reduce power to the catheter heating element while the catheter is in the patient's body if the temperature of the heating element is rising in such a fashion as to indicate that it will reach a predetermined maximum level.

It is a further object of the invention to reduce power to the system while the catheter is in the patient's body if power is being unintentionally applied to the calibration circuitry instead of the heating element.

It is a further object of the invention to reduce power to the heating element if power is unintentionally provided to the heating element during a calibration regimen while the catheter is outside the patient's body.

To achieve the above-referenced and other objects of the invention not specifically set forth, a system according to a first aspect of the invention for controlling power to the heating element of a thermodilution catheter comprises a thermodilution catheter having a heating element, means for supplying and controlling power to the heating element, means for monitoring the temperature of the heating element, means for determining the rate of change of the temperature of the heating element and means responsive to the rate of temperature change measurement to control the power supplying means to remove power from the heating element.

In one preferred embodiment, the heating element is a resistive heater with a known characterized resistance and a known temperature coefficient of resistance and the temperature monitoring means comprises means for monitoring the resistance of the heating element. In another preferred embodiment, the monitoring means further comprises means for measuring the current applied to the heating element. Alternatively, the heating element could be monitored by having a dedicated thermistor or thermometer which is used in conjunction with the heating element.

According to a second aspect of the invention, a system for controlling power to the heating element of a thermodilution catheter comprises a thermodilution catheter having a heating element, a calibration circuit, means for controlling the supply of power to the system, means for switching power between the calibration circuit or the heating element, means for determining whether power has been supplied to the calibration circuit, and means responsive to the calibration circuit monitoring means to remove power from the system.

In a preferred embodiment, the calibration circuit is a resistor, the power supply switching means comprises a switch between the calibration circuit and the heating element, and the means for monitoring the supply of power to the calibration circuit is means for sensing the voltage across the resistor. In an alternate, preferred embodiment, the means for monitoring the supply of power to the calibration circuit further comprises means for determining the rate of change of the temperature of the heating element.

A method according to a third aspect of the invention for controlling power to the heating element of a thermodilution catheter includes the steps of (1) supplying and controlling power to the heating element, (2) monitoring the temperature of the heating element, (3) determining the rate of change of the temperature of the heating element, and (4) controlling the power supplied to the heating element in response to the rate of temperature change determination.

A method according to a fourth aspect of the invention for controlling power to the heating element of a thermodilution catheter includes the steps of (1) supplying power either to the calibration circuit or the heating element, (2) monitoring the supply of power to the calibration circuit, and (3) removing power from the system in response to monitored calibration circuit.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described certain preferred embodiments of the invention.

DETAILED DESCRIPTION OF THE PREFERRED EMBODIMENT(S)

A system in accordance with preferred exemplary embodiments of the invention will be described below in detail with reference to FIGS. 1–8. It will be appreciated by those of ordinary skill in the art that the description given herein with respect to those embodiments is for exemplary purposes only and is not intended in any way to limit the scope of the invention. All questions regarding the scope of the invention may be resolved by referring to the appended claims.

Figure 1:
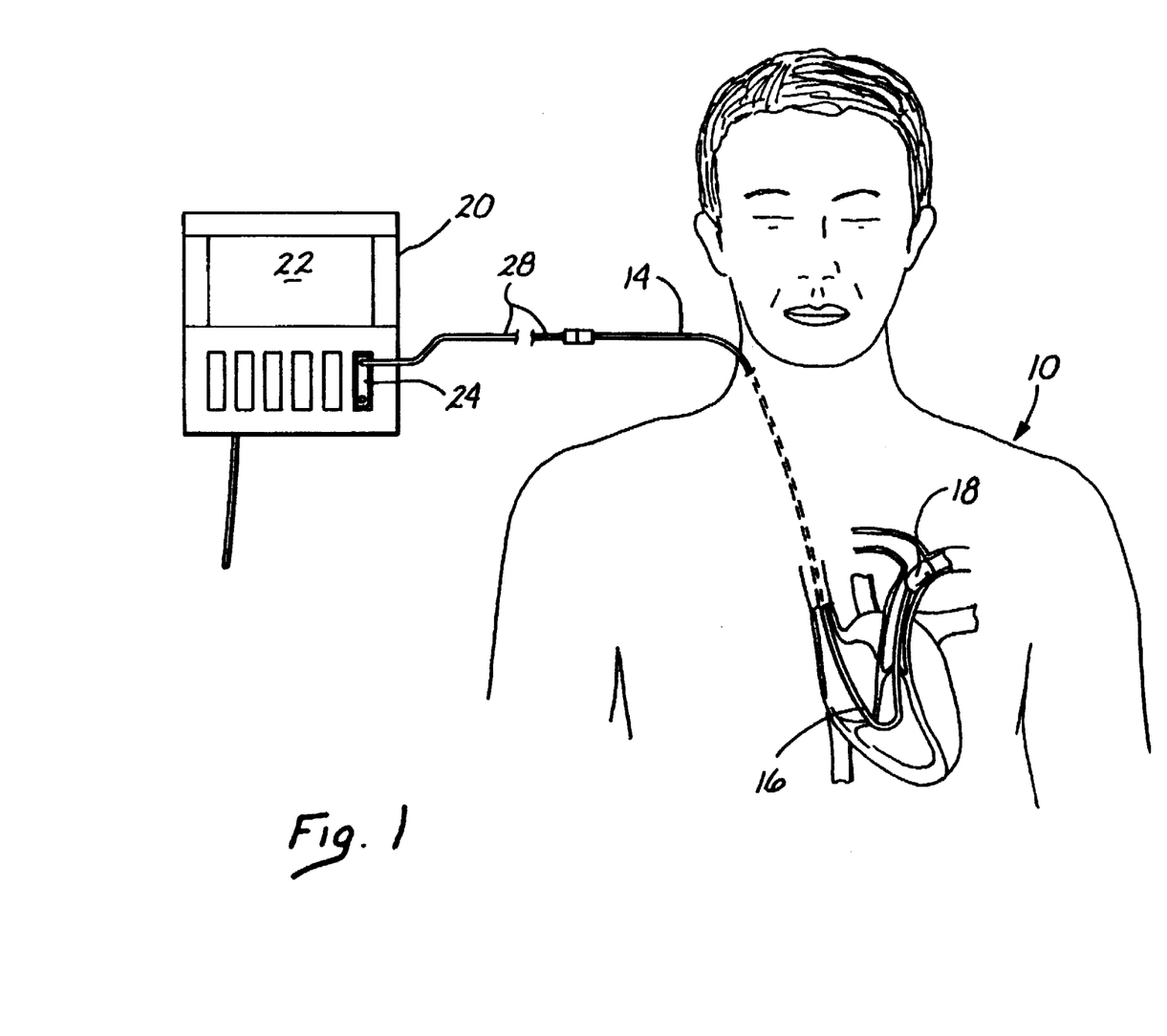
FIG. 1 illustrates a fragmentary and somewhat schematic view of a human patient with a thermodilution catheter having a heating element placed in the patient's right heart, and a monitoring apparatus associated with this catheter.

A detailed description of pulmonary artery catheters, and thermodilution catheters in particular, is not given herein, for the features of such catheters are well known to those familiar to the art. FIG. 1 shows a human patient 10, within whose right heart 12 has been placed a thermodilution catheter 14 having a heating element 16. The catheter has a flotation balloon 18 at its distal end and it is placed according to techniques known to those skilled in the art. Externally of the patient 10, the catheter 14 is connected to a monitor 20 which includes a display screen 22 upon which information about the patient's condition can be displayed. In a preferred exemplary embodiment, as shown in FIG. 1, catheter 14 is connected to a module 24, which contains the continuous cardiac output ("CCO") measurement subsystem. Module 24 can be inserted into various monitors such as monitor 20, which is configured to receive various modules 24, each of which is adapted to monitor certain patient physiological parameters. The modularity of the CCO measurement subsystem allows it to be moved around the hospital to various bedside locations. The configuration of monitor 20 allowing it to receive various modules permits various types of patient information to be integrated into one monitor and also permits such information to be provided to a remote location, such as to a nurse's station, central patient monitoring and data recording computer system, or to a physician who may wish to receive the information at his home or office via a telephone line interconnection with such a hospital's central patient monitoring computer system.

Figure 2:
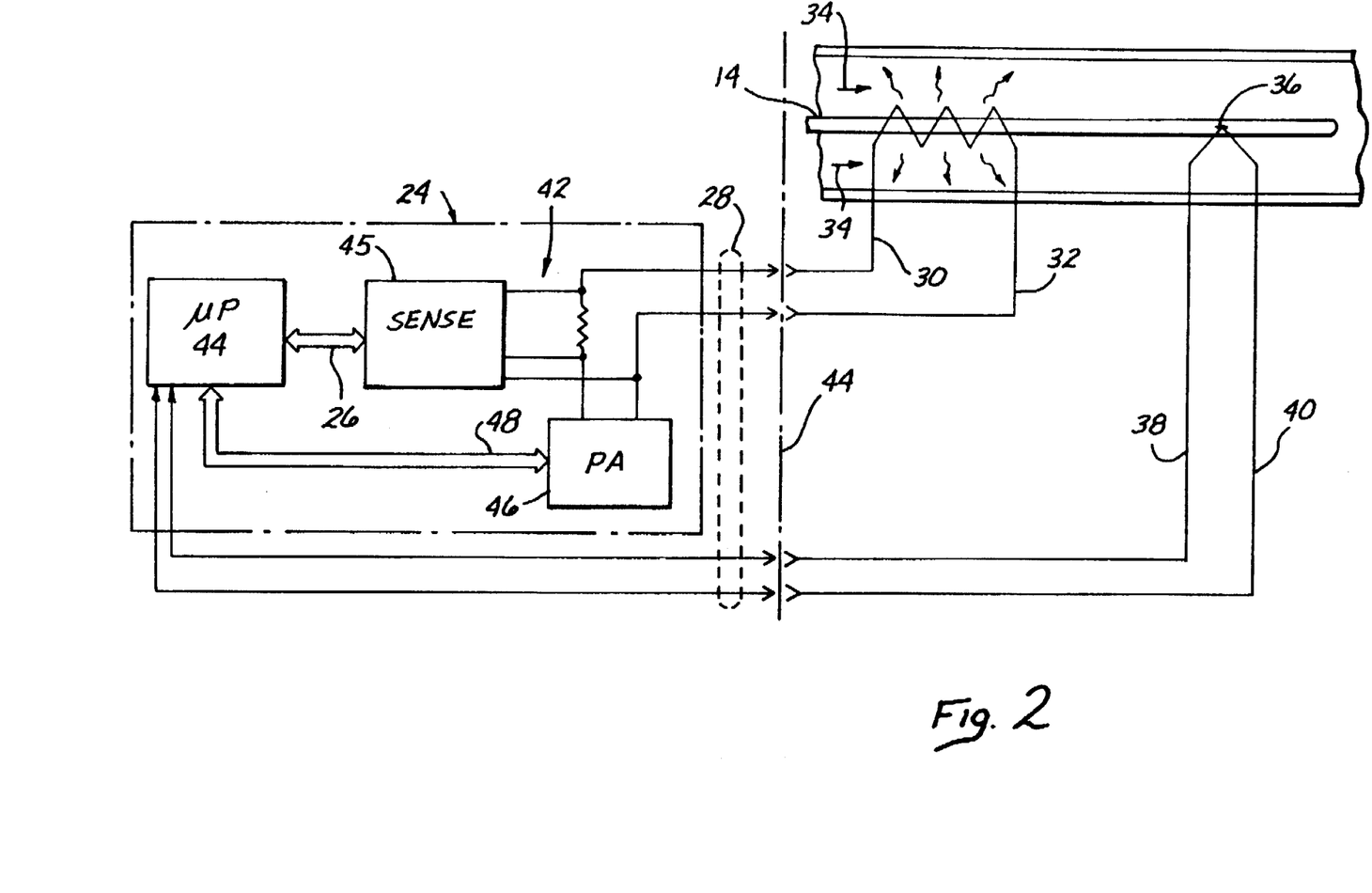
FIG. 2 is a schematic depiction of the functional interaction between the thermodilution catheter and the modular embodiment of the control system of the present invention.

With attention now to FIG. 2, which illustrates the modular embodiment of the present invention, it is seen that module 24 has connection to monitor 20 via a data bus, generally indicated by the double-headed arrow 26, and via a number of electrical connections which supply electrical power to module 24 from monitor 20. It will be appreciated that FIG. 2 is very schematic, and that the electrical conductors depicted outwardly of catheter 14 are actually of a fine gauge and over a portion of their length are disposed within the elongate and comparatively thin shaft of the catheter. Another portion of the length of the illustrated conductors will be understood to be provided by cable 28. In this embodiment, two of the conductors 30 and 32 connect to heating element 16 which is outwardly disposed on the distal end portion of catheter 14. In a preferred, exemplary embodiment, heating element 16 may be configured as a flexible thin metallic film element having a known impedance characteristic and a high coefficient of resistance change with change in temperature. Catheter 14 will preferably be configured so that heating element 16 is actually disposed in the right ventricle of patient 10. The turbulent blood flow in this ventricle resulting from the pumping action of the heart assists in distributing heat energy from heating element 16 uniformly throughout the pulmonary blood flow. Downstream of heating element 16 with respect to the direction of blood flow (indicated with arrows 34) is disposed a temperature measuring sensor 36. Sensor 36 may be a small bead thermistor, for example, and is connected to cable 28 and monitor 20 via conductors 38 and 40.

Within module 24, conductors 38 and 40 supply the temperature signal from sensor 36 to a microprocessor based control system 42, which includes microprocessor 44 and sense circuit 45. Sense circuit 54 converts output voltage and current into digital data for microprocessor 44. In a preferred, exemplary embodiment, sense circuit 44 includes a differential amplifier and an RMS convertor (not shown).

In a preferred, exemplary embodiment, control system 42 includes power amplifier circuit 46. Microprocessor 44 has a two-way control and data interface with power amplifier circuit 46, as is generally indicated by the control and data bus arrow 48. This general interface reference numeral (48) will be used in various places throughout the following explanation to refer to the interface of information and control signals in one or both directions between power amplifier 46 and microprocessor 44.

In the prior art system of Quinn et al, referenced above, the heating element communicates with a cardiac output computer which receives power level signals for controlling the heating element. By using a heating element comprised of material which has a high temperature coefficient of resistance, not only can it be used as a heat supplier, but it can also serve as its own temperature sensing device according to the principles outlined in Quinn et al.

By using a power source of a controlled voltage amplitude, and by measuring blood temperature, an increasing catheter heating element temperature can be directly detected as an increasing heating element resistance which reduces the power delivered to the heating filament. In this manner, the actual current and voltage to the catheter heating element can be continuously monitored and thereby controlled. Thus, during operation the cardiac output computer may continuously measure and monitor the temperature of the heating element to keep it within a predetermined safe limit.

Figure 3:
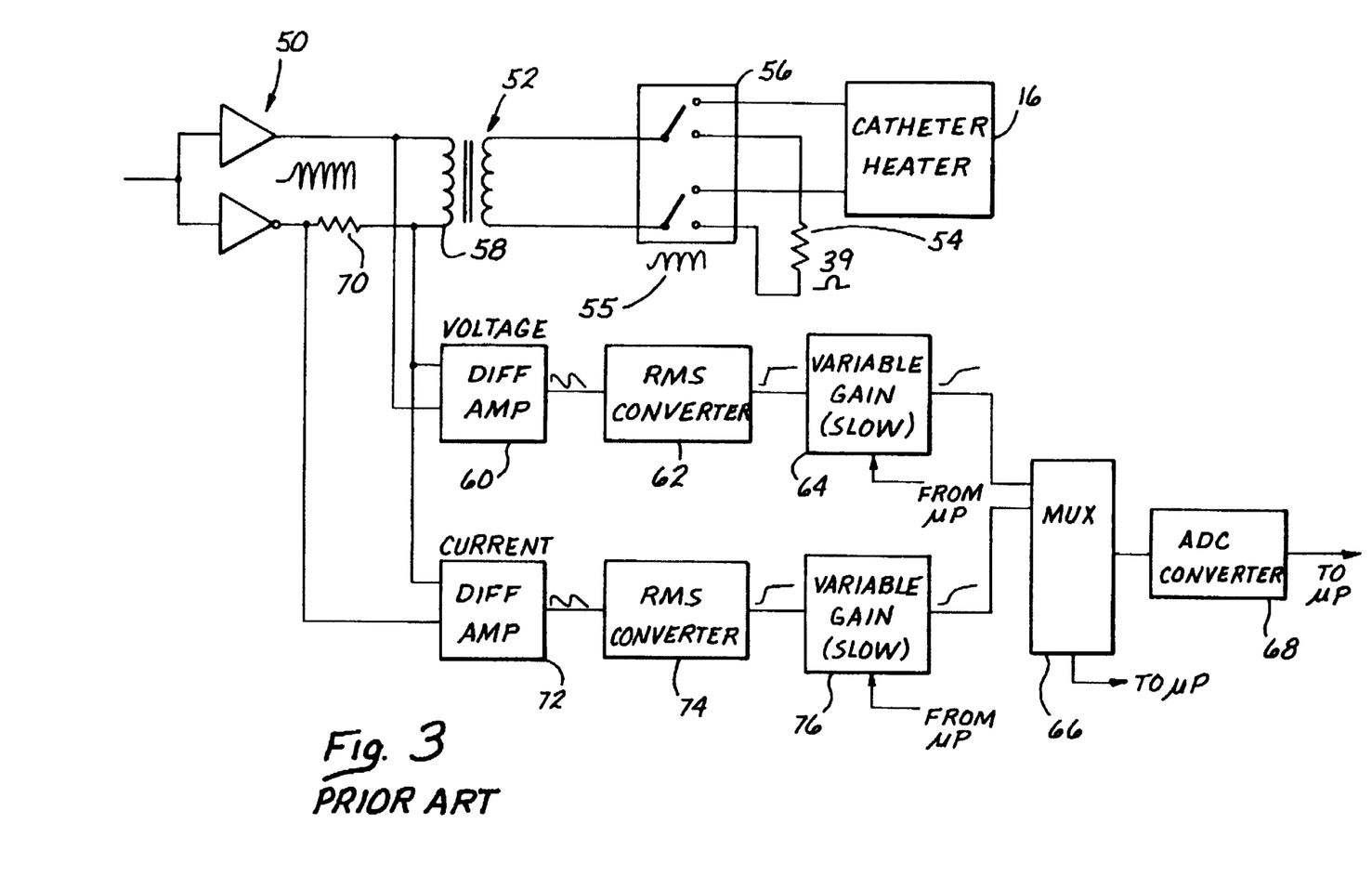
FIG. 3 is a schematic block diagram of a prior art thermodilution catheter heating element control system.

FIG. 3 illustrates a prior art control system which embodies the teachings of Quinn et al. This system was embodied in the VIGILANCE® cardiac output monitor marketed and sold by Baxter Healthcare Corporation, a subsidiary of Baxter International, Inc., the assignee of the present invention. As seen in FIG. 3, drive amp 50 drives a desired sinusoidal signal across isolation transformer 52 to the isolated patient-connected section of the system which includes heating element 16 of catheter 14, and a calibration resistor 54. The isolated patient-connected section includes relay control 55 which can send the signal either to heating element 16 or to calibration resistor 54 via relay 56.

In order to effectively control the heating element temperature, the VIGILANCE® cardiac output system includes a current monitoring subunit and a voltage monitoring subunit supplied to heating element 16. The voltage monitoring subunit is connected across the primary winding 58 of isolation transformer 52 and comprises differential amp 60, RMS convertor 62 and microprocessor controlled, variable gain, filtered potentiometer 64.

Differential amp 60 in the voltage measuring subunit is used to scale the signal down to an appropriate voltage level for monitoring purposes. RMS convertor 62 then demodulates by converting the AC signal to a DC signal. The signal is again scaled by variable potentiometer 64 which sends it to multiplexer switch 66. Switch 66 sends the signal to Analog to Digital Convertor ("ADC") 68 where it is converted to a digital signal and sent on to microprocessor 44 (not shown).

The current monitoring subunit is connected across sense resistor 70 to draw current for monitoring purposes and comprises differential amp 72, RMS convertor 74 and low pass gain stage 76. In the VIGILANCE® cardiac output monitor, gain stage 76 includes a low pass filtered inverting op amp circuit with a programmable resistor. Differential amp 72 is used to scale the signal up to an appropriate voltage level for monitoring purposes. RMS convertor 74 then demodulates by converting the AC signal to a DC signal. Gain stage 76 scales the signal and sends it to multiplexer switch 66. As described above with respect to the voltage monitoring subunit, the signal is sent to ADC convertor 68 where it is converted to a digital signal and sent on to microprocessor 40 (not shown).

As discussed above with respect to the Quinn et al. system, the aforementioned control system provides a fail-safe control wherein the temperature of heating element 16 can be monitored such that power can be removed from heating element 16 when some absolute temperature threshold is met. However, there are circumstances where it would be helpful to also monitor the rate of change of the heating element temperature in order to provide either a fault tolerant or a faster fail-safe system.

Furthermore, during a calibration regimen, relay control 56 sends the signal to calibration resistor 54 to calibrate the system. It would be helpful to be able to determine whether relay control 55 has failed and whether power has been supplied to heating element 16 during the calibration regimen. This is not always a safety issue per se, since many calibration regimens occur prior to catheter 14 being inserted into patient 10. However, if power is applied to heating element 16 while catheter 14 is in air, the catheter tubing could be thermally deformed. The prior art system of Quinn et al. includes means to determine whether the catheter is in air by measuring the temperature of heating element 16 to determine whether it exceeds some absolute value for more than a specified integrated time temperature product. This is done, however, without regard to whether power is being applied to calibration resistor 54.

Figure 4:
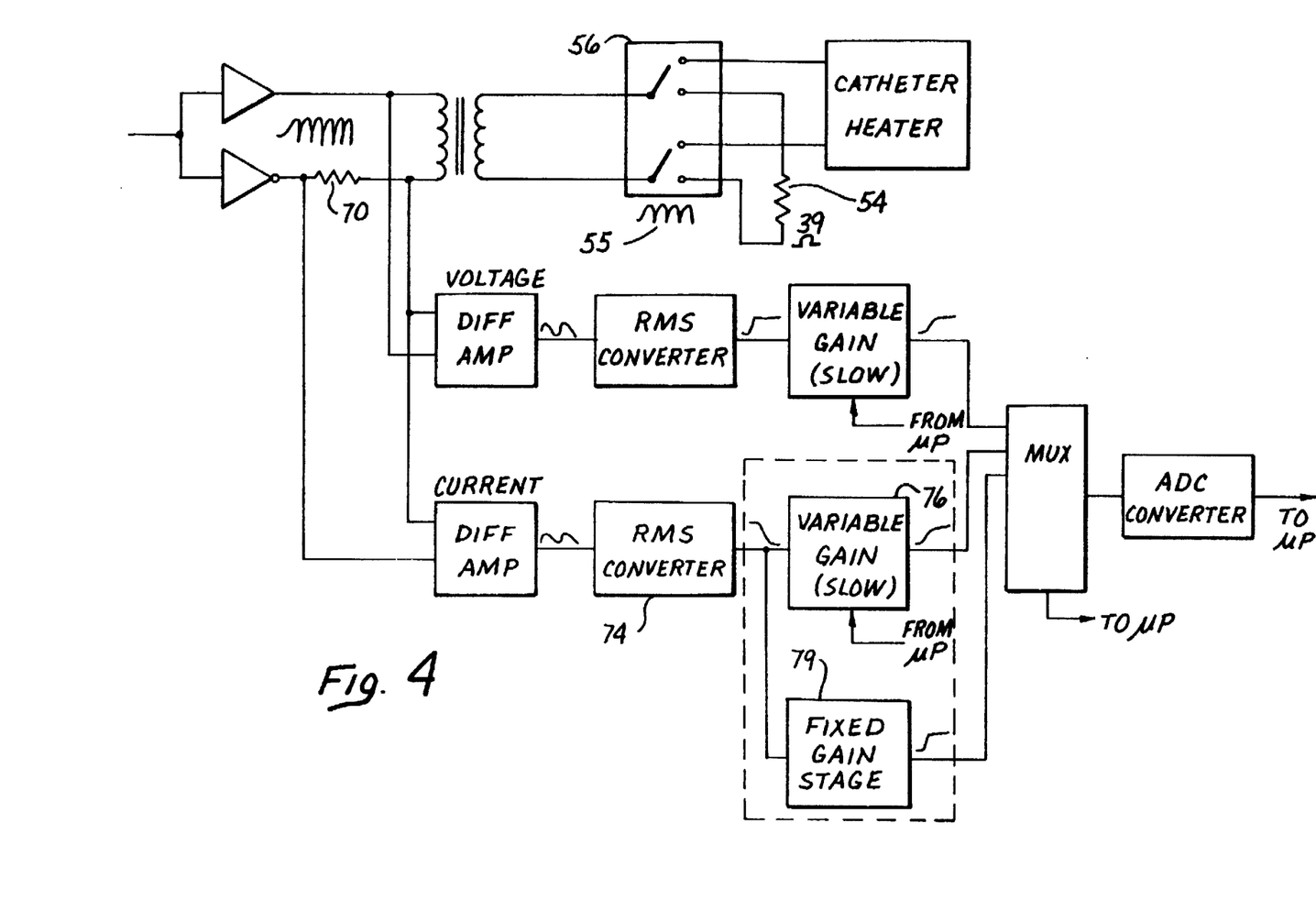
FIG. 4 is a schematic block diagram of an exemplary, preferred embodiment of the thermodilution catheter heating element control system of the present invention.

FIG. 4 illustrates a exemplary, preferred embodiment of the thermodilution catheter heating element control system of the present invention. This embodiment comprises means for determining the rate of change of the temperature of the heating element. In particular, this embodiment utilizes dual bandwidth sensing circuit 78 which comprises gain stage 76 and unfiltered fixed gain circuit element 79. Fixed gain element 79 scales the current signal coming from RMS convertor 74. Fixed gain element 79 could comprise a non-filtering inverting op amp. This would provides a current signal with an appropriate bandwidth to permit microprocessor 44 to calculate the rate of change of the temperature of heating element 16. Alternatively, those skilled in the art would recognize that other circuit elements could be substituted for the op amp, such as multipliers, transistorized amplifiers, and filters, to generate the appropriate signal(s). By calculating the rate of change of temperature of heating element 16, control of the heating element can be accomplished in a shorter period of time. Specifically, if the rate of change exceeds a certain predetermined value, the system can withdraw power from heating element 16 prior to it reaching its predetermined temperature threshold. The present invention accomplishes this without the need for a blood temperature measurement and without a system calibration. This was not possible in the prior art Quinn et al. system due to the structure of the current monitoring subunit.

Figure 5:
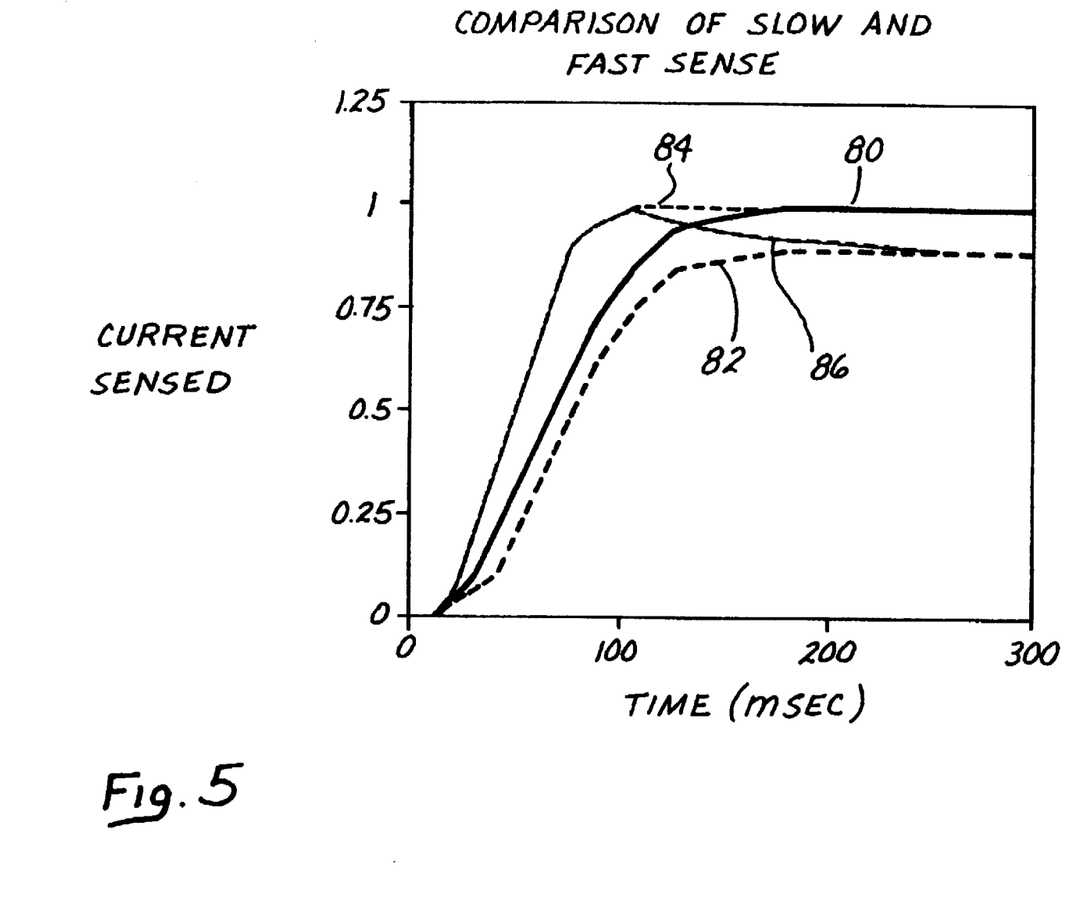
FIG. 5 is a graph of current versus time curves illustrating the differences between a prior art control system and the control system of the present invention.

The advantages of the aforementioned embodiment of the present invention will become more evident upon review of FIG. 5, which graphically illustrates sensed current (i) versus time (t) curves for the prior art system and for the present invention. Curves 80 and 82 graphical represent the sensed current/time relationship in the prior art system. Since the system utilizes a constant voltage source and a resistive heater, any change in current would indicate a change in resistance, since, given a constant voltage, the current and the resistance are inversely proportional. Furthermore, a change in resistance value indicates a change in temperature, since resistance and temperature are directly proportional, as a consequence of the positive coefficient of resistance of the heating element. Hence, any reduction in current from the threshold value would indicate an increase in temperature. In curves 80 and 82 the sensed current rises to a threshold value and then stabilizes. Since curves 80 and 82 indicate a constant current upon reaching the threshold value, the heating element temperature appears to remain constant. However, curve 82 indicates a lower current value which is indicative of a higher temperature for heating element 16. In this case the heating element temperature has reached the maximum operating temperature without providing any advance warning.

Curves 84 and 86 graphically illustrate the sensed current/time relationship in the present invention. Curve 84 illustrates the situation wherein the sensed current rises to a threshold value and then stabilizes. Again, since curve 80 indicates a constant current upon reaching the threshold value, the heating element temperature appears to remains constant. Curve 86 graphically illustrates the sensed current/time relationship in the present invention wherein there is a noticeable drop in the current, indicating a precipitous rise in the temperature of heating element 16.

A review of curves 82 and 86 will illustrate important differences between the prior art system and the present invention. Both curves reach a particular current value, at about 250 msec, which indicates a maximum temperature for heating element 16. However, curve 82 reached its current level gradually and gave no advance warning. Curve 86, in the other hand, began its descent around the 100 msec point. Curve 86 provided rate of temperature change information which would permit microprocessor 44 to control the provision of power to heating element 16. Thus, power could be withdrawn from heating element prior to the time it reached it maximum allowable value.

The teachings herein will enable those skilled in the art to make other embodiments which fall within the principles of the present invention. For example, a patient side circuit which functions to obtain a high bandwidth current signal could also be utilized to derive a rate of change temperature measurement along the lines discussed above.

Figure 6:
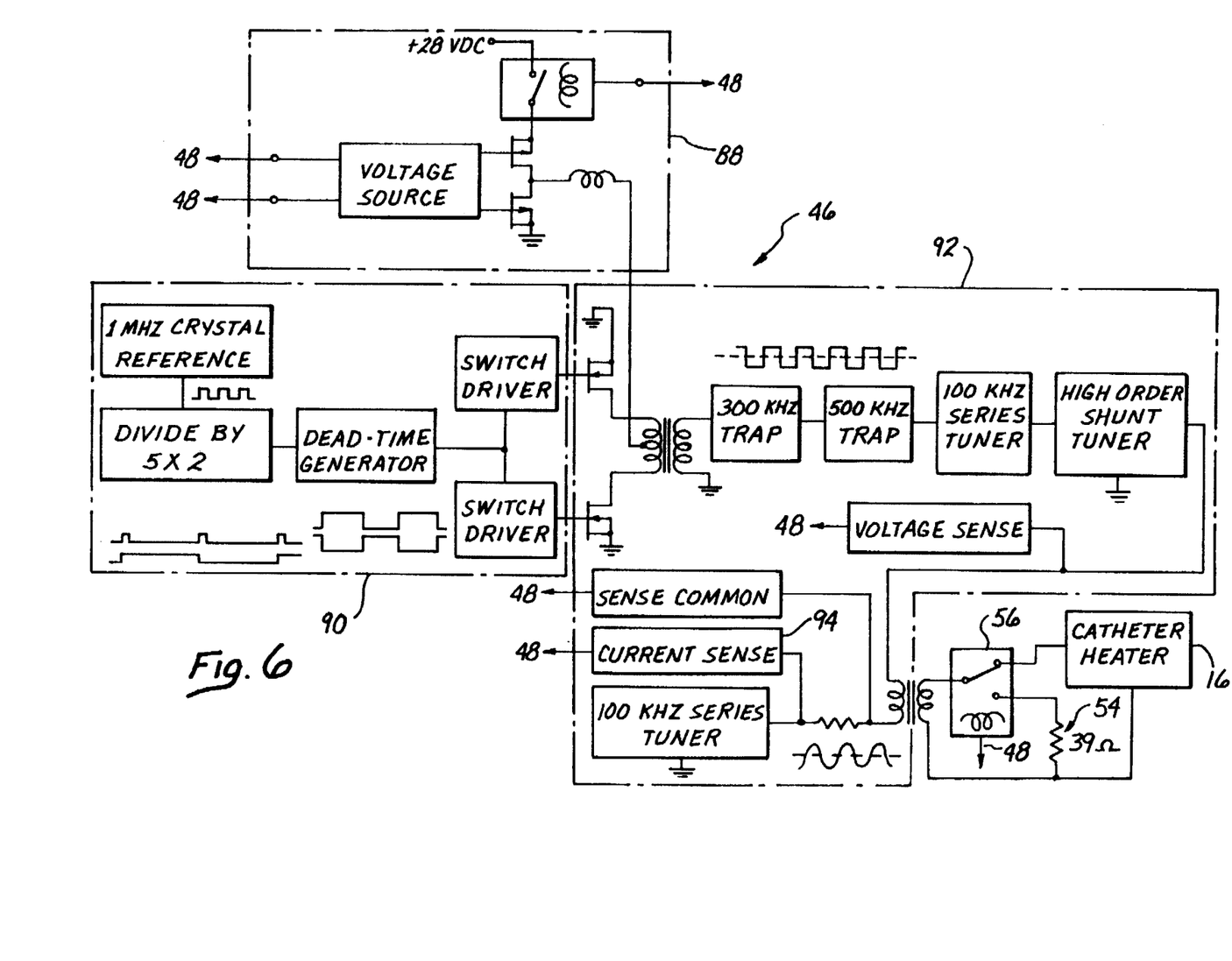
FIG. 6 is a schematic block diagram of another exemplary, preferred embodiment of the thermodilution catheter heating element control system of the present invention.

Another exemplary, preferred embodiment is illustrated in FIG. 6. This embodiment is particularly suited to the module version of the CCO measurement subsystem illustrated in FIG. 2. FIG. 6 illustrates power amp 46 of FIG. 2 in greater detail. Power amp 46 comprises variable voltage source 88, frequency source 90 and switch-mode amp section 92. In other embodiments, a linear amplifier could be used in place of amp section 92. As indicated above, arrows 48 indicate interfacing with microprocessor 44. The functioning of these components is more fully set forth in parent U.S. application Ser. No. 08/268,217, which has been incorporated herein by reference as though fully set forth. Switch-mode amp section comprises current sense 94 which interfaces with microprocessor 44 along interface 48. Current sense 94 functions in a similar fashion as fixed gain circuit element 79 of FIG. 4 to provide a current signal with an appropriate bandwidth to permit microprocessor 44 to calculate the rate of change of the temperature of heating element 16. In an exemplary, preferred embodiment, current sense 94 includes a differential amplifier and an RMS convertor with sufficient precision and bandwidth to generate the appropriate signal without variable gain elements.

In an alternate embodiment (not shown) the temperature of heating element 16 is sensed separately with a contiguous thermometer or thermistor dedicated for the purpose. In this embodiment, the temperature of the heating element would be continuously monitored by the thermometer or thermistor and this information would be provided to microprocessor 40 for calculation of the rate of change of the heating element temperature for an early warning of a rising heating element temperature and further control of the provision of power along the lines discussed above. Furthermore, the use of a resistive heating element could be used in conjunction with a contiguous thermometer or thermistor to provide a redundant monitoring capacity.

Figure 7:
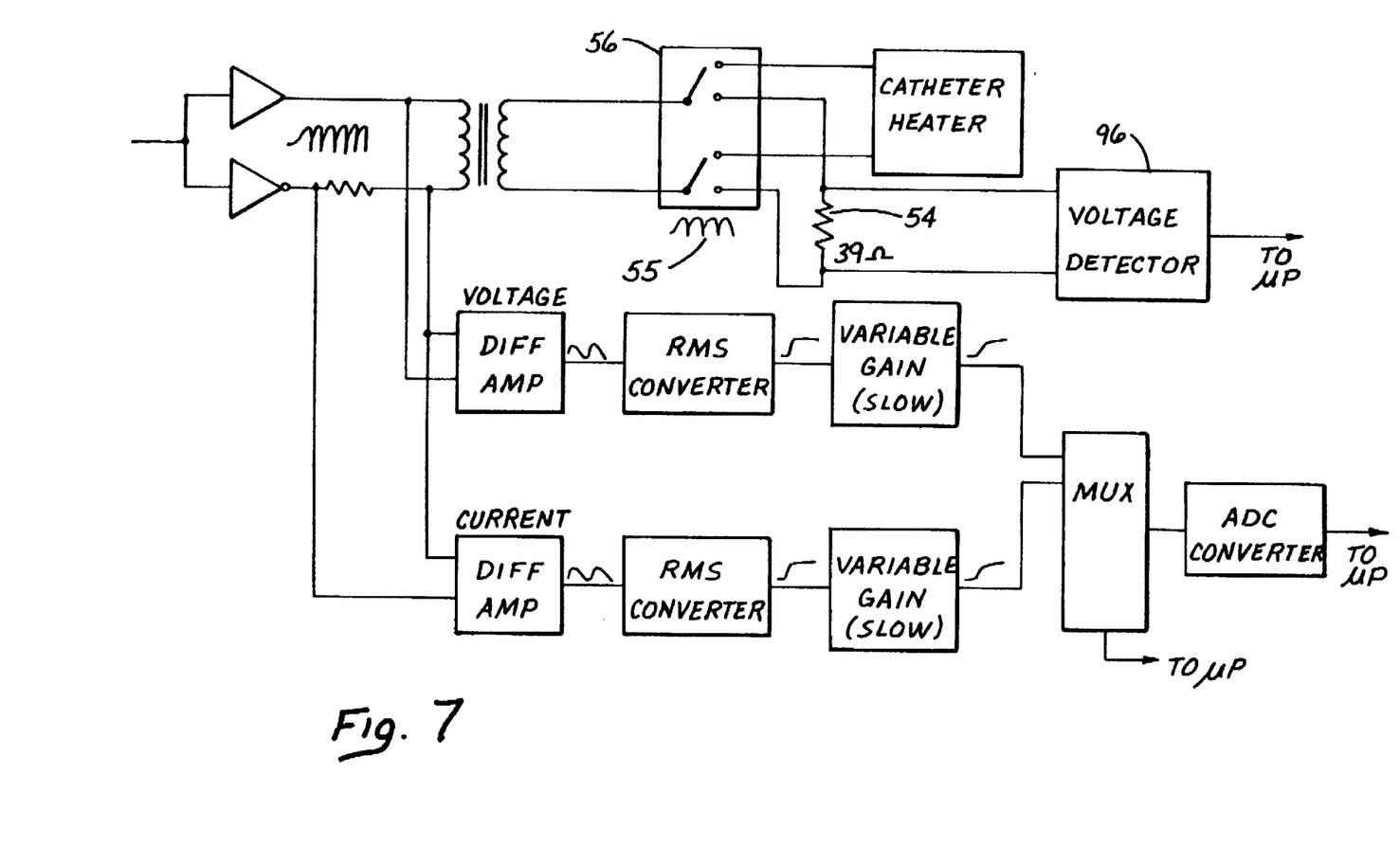
FIG. 7 is a schematic block diagram of yet another exemplary, preferred embodiment of the thermodilution catheter heating element control system of the present invention.

Another exemplary, preferred embodiment of the present invention is illustrated in FIG. 7. In this embodiment, which is yet another modification of the VIGILANCE® cardiac output monitor discussed above, voltage detector 96 senses voltage across calibration resistor 54 in order to determine whether power has been transmitted to resistor 54 or to heating element 16. Those skilled in the art will appreciate the various circuit elements available to sense voltage across resistor 54. In an exemplary, preferred embodiment, a MOSFET or a Darlington transistor is used with a half-wave rectifier and filter.

The embodiment of FIG. 7 is particularly useful just prior to the calibration of the VIGILANCE® system, wherein power is supplied to a calibration circuit while the catheter is outside of the patient's body. If there is a failure in relay control 56, power could inadvertently be supplied to heating element 16 while the catheter is under a zero flow condition outside the patient's body, resulting in thermal deformation of the catheter tubing. By sensing the voltage across resistor 54, power to heating element 16 can be removed, preventing damage to catheter 14. This embodiment also provides the information, while the catheter is in the patient's body, that power being applied to the system is not going to heating element 16, but is instead going to calibration resistor 54.

Figure 8:
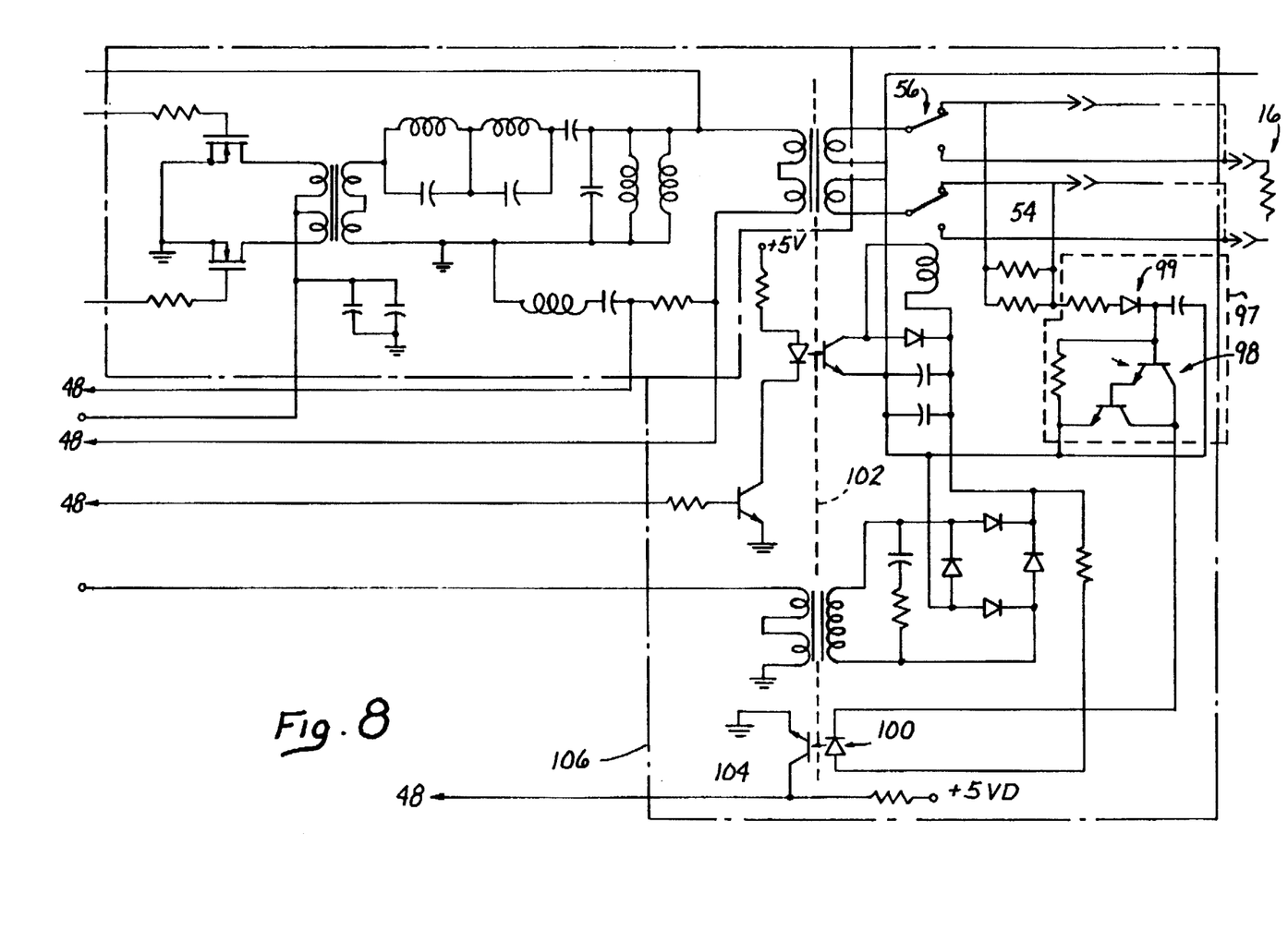
FIG. 8 is a schematic block diagram of yet another exemplary, preferred embodiment of the thermodilution catheter heating element control system of the present invention.

Yet another exemplary, preferred embodiment of the thermodilution catheter heating element control system of the present invention is illustrated in FIG. 8. This embodiment also relates to the module version of the CCO measurement subsystem illustrated in FIG. 2. In this embodiment, the voltage occurring across calibration resistor 54 is used to drive transistorized voltage detector circuit 97 into conductivity. In this embodiment, circuit 97 utilizes Darlington transistor 98 with a half-wave rectifier and filter 99. Note that in this embodiment, calibration resistor 54 is in fact formed by two resistors connected in parallel. Conductivity at switching circuit 98 illuminates an LED 100. Light from LED 100 is beamed across patient isolation barrier 102 and illuminates photodiode 104, causing it to become conductive. Conductivity of photodiode 104 pulls low the signal on conductor 106, which has connection with microprocessor 44, as is indicated by interface arrow 48. Thus, microprocessor 44 is informed that power is being dissipated through calibration resistor 54, and not heating element 16. This provides the same advantages discussed above with respect to the embodiment of FIG. 7.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A system for monitoring and controlling a temperature of a catheter mounted heating element, comprising:
   a thermodilution catheter having a heating element;
   a calibration circuit means;
   means for controlling the supply of power to the system;
   means for switching power between said calibration circuit and the heating element;
   means for determining whether power has been supplied to said calibration circuit; and
   means responsive to the power determining means to remove power from the system.

2. The system of claim 1 wherein said calibration circuit means comprises a resistor.

3. The system of claim 2 wherein said means for monitoring the supply of power to said calibration circuit comprises means for measuring a voltage across said resistor.

4. The system of claim 1 wherein said switching means comprises a relay between said calibration circuit and the heating element.

5. The system of claim 1 wherein said calibration circuit means comprises at least two resistors connected in parallel.

6. The system of claim 5 further comprising a means for detecting voltage across said resistors.

7. The system of claim 6 wherein said voltage detecting means comprises a transistorized voltage detecting circuit.

8. The system of claim 7 wherein said transistorized voltage detecting circuit further comprises an isolated power source, a transistor connected to said isolated power source, an LED connected to said transistor for emitting light upon activation by said transistor, and a photodiode in electrical communication with said power removing means, wherein light emitted by said LED is received by said photodiode.

9. The system of claim 8 wherein said transistor is a MOSFET and wherein said transistorized circuit further comprises a half-wave rectifier and a filter.

10. The system of claim 8 wherein said transistor is a Darlington transistor and wherein said transistorized circuit further comprises a half-wave rectifier and a filter.

11. The system of claim 1 wherein said power determining means comprises means for determining the rate of change of the temperature of the heating element.

12. The system of claim 11 wherein said means for determining the rate of change of the temperature of the heating element comprises a current sensing means.

13. The system of claim 12 wherein said current sensing means comprises a dual bandwidth sensing circuit means.

14. The system of claim 13 wherein said dual bandwidth sensing circuit means further comprises a fixed gain stage circuit means.

15. The system of claim 14 wherein said fixed gain stage circuit means comprises a non-filtering inverting op amp.

16. The system of claim 12 wherein said current sensing means comprises a high bandwidth sensing circuit means.

17. A method of monitoring and controlling a temperature of a thermodilution catheter mounted heating element, comprising the steps of:
    providing a calibration circuit means;
    switching a supply of power either to the calibration circuit means or to the heating element;
    monitoring the supply of power to the calibration circuit; and
    removing power from either the calibration circuit or the heating element in response to the monitored power at the calibration circuit means.

18. The method of claim 17 wherein the calibration circuit means comprises at least one resistor and wherein said power monitoring step comprises the step of measuring the voltage across the calibration circuit means.

19. The method of claim 17 further comprising providing a transistorized voltage detecting circuit having an isolated power source, wherein said switching step comprises the step of using said transistorized voltage detecting circuit to switch power between the calibration circuit and the heating element.

20. The method of claim 19 further comprising providing a MOSFET circuit having an isolated power source, a MOSFET, and a half-wave rectifier and filter, wherein said switching step comprises the step of using said MOSFET circuit to switch power between the calibration circuit and the heating element.

21. The method of claim 19 further comprising providing a Darlington circuit having an isolated power source, a Darlington transistor, and a half-wave rectifier and filter, wherein said switching step comprises the step of using said Darlington circuit to switch power between the calibration circuit and the heating element.

22. The method of claim 19 wherein said switching step comprises the steps of activating an LED in response to the monitored power, using the LED to illuminate a photodiode and using the photodiode to switch power between the calibration circuit and the heating element.

23. The method of claim 17 wherein said power supply monitoring step further comprises the step of determining the rate of change of the temperature of the heating element.

24. The method of claim 23 wherein said rate of change determination step comprises sensing current applied to the heating element.

25. The method of claim 23 further comprising providing a dual bandwidth sensing circuit, wherein said rate of change determination step comprises using said dual bandwidth sensing circuit to sense current applied to the heating element.

26. The method of claim 23 further comprising providing a fixed gain stage circuit, wherein said rate of change determination step comprises using said fixed gain stage circuit to sense current applied to the heating element.

27. The method of claim 23 further comprising providing a non-filtering inverting op amp, wherein said rate of change determination step comprises using said non-filtering inverting op amp to sense current applied to the heating element.

28. The method of claim 23 further comprising providing a high bandwidth sensing circuit, wherein said rate of change determination step comprises using said high bandwidth sensing circuit to sense current applied to the heating element.

* * * * *